US012773346B2

(12) United States Patent
Malhotra et al.

(10) Patent No.: US 12,773,346 B2
(45) Date of Patent: Oct. 27, 2026

(54) INCISION GUIDE TOOL FOR OCULAR DEVICE IMPLANTATION AND METHODS OF USE

(71) Applicant: Genentech, Inc., South San Francisco, CA (US)

(72) Inventors: Varun Kumar Malhotra, South San Francisco, CA (US); Christopher Arena, South San Francisco, CA (US); Giulio Barteselli, South San Francisco, CA (US); Alexandra Rose Cole, Oakland, CA (US); Natalia Fijalkowski Callaway, South San Francisco, CA (US); Adam Daniel Farchone, San Jose, CA (US); Carl C. Awh, South San Francisco, CA (US); Signe Ruth Erickson, South San Francisco, CA (US); Eric Bass, Chesterfield, MO (US); Renato Justo Ordonez, Chesterfield, MO (US); Gregg Scheller, Chesterfield, MO (US)

(73) Assignee: Genentech, Inc., South San Francisco, CA (US)

( * ) Notice: Subject to any disclaimer, the term of this patent is extended or adjusted under 35 U.S.C. 154(b) by 65 days.

(21) Appl. No.: 18/908,575

(22) Filed: Oct. 7, 2024

(65) Prior Publication Data

US 2025/0025336 A1 Jan. 23, 2025

Related U.S. Application Data

(63) Continuation of application No. PCT/US2023/017929, filed on Apr. 7, 2023.
(Continued)

(51) Int. Cl.
*A61F 9/007* (2006.01)
*A61B 17/32* (2006.01)
*A61B 17/3209* (2006.01)

(52) U.S. Cl.
CPC .. *A61F 9/007* (2013.01); *A61B 2017/320052* (2013.01); *A61B 17/3209* (2013.01)

(58) Field of Classification Search
CPC ..... A61B 17/3209; A61B 2017/320052; A61F 9/0017; A61F 9/007; A61F 9/00739; A61F 9/00754; A61F 9/00781
(Continued)

(56) References Cited

U.S. PATENT DOCUMENTS

D255,490 S 6/1980 Pastrick
4,520,815 A * 6/1985 Marinoff .............. A61F 9/0133 606/166
(Continued)

FOREIGN PATENT DOCUMENTS

CN D306338188 S 2/2021
EP 3 636 230 A1 4/2020
(Continued)

OTHER PUBLICATIONS

IOPtimaVideos. (Sep. 2, 2019). Flapper by IOPtima [video]. YouTube. https://www.youtube.com/watch?v=2wkoBBgfucY. 1 Page.
(Continued)

*Primary Examiner* — Jocelin C Tanner
(74) *Attorney, Agent, or Firm* — FBT Gibbons LLP

(57) ABSTRACT

A device configured to guide creation of an incision in a sclera of an eye including an elongate handle and a footplate having a plurality of struts defining a central opening extending between an upper surface and a lower surface of the footplate. A first strut of the plurality of struts has a proximal-facing blade guide surface that is straight and
(Continued)

extends between two lateral struts of the plurality of struts. A second strut of the plurality of struts has a proximal-facing limbal guide surface that is curved. The blade guide surface is separated a distance from the limbal guide surface to identify a target location for creating an incision relative to a limbus of the eye. The blade guide surface has a length between the two lateral struts that limits a length of the incision that can be created using a cutting blade inserted through the central opening.

34 Claims, 8 Drawing Sheets

Related U.S. Application Data

(60) Provisional application No. 63/329,277, filed on Apr. 8, 2022.

(58) Field of Classification Search
USPC .................................................. 606/167, 107
See application file for complete search history.

(56) References Cited

U.S. PATENT DOCUMENTS

| | | | |
|---|---|---|---|
| 4,688,570 A | 8/1987 | Kramer et al. | |
| D296,926 S | 7/1988 | Heasley | |
| 4,880,017 A | 11/1989 | Soll et al. | |
| 5,006,123 A | 4/1991 | Soll et al. | |
| D372,309 S | 7/1996 | Heldreth | |
| D373,634 S | 9/1996 | Brown | |
| 5,653,723 A | 8/1997 | Kamerling et al. | |
| D427,678 S | 7/2000 | Koros et al. | |
| D439,976 S | 4/2001 | Cote | |
| D443,359 S | 6/2001 | Nathanson et al. | |
| D511,383 S | 11/2005 | Stanger | |
| 7,935,123 B2 | 5/2011 | Fanger et al. | |
| D644,735 S | 9/2011 | Elbe et al. | |
| D658,285 S | 4/2012 | Ryshkus et al. | |
| D695,897 S | 12/2013 | Splieth et al. | |
| 2003/0014036 A1 | 1/2003 | Varner et al. | |
| 2007/0212397 A1 | 9/2007 | Roth | |
| 2010/0137692 A1 | 6/2010 | Lindsay et al. | |
| 2010/0255061 A1 | 10/2010 | de Juan, Jr. et al. | |
| 2012/0046680 A1* | 2/2012 | Dishler | A61F 9/007 606/166 |
| 2012/0095439 A1 | 4/2012 | de Juan, Jr. et al. | |
| 2013/0165860 A1 | 6/2013 | Doud et al. | |
| 2013/0274691 A1 | 10/2013 | de Juan, Jr. et al. | |
| 2013/0274692 A1 | 10/2013 | Alster et al. | |
| 2013/0324918 A1 | 12/2013 | de Juan, Jr. et al. | |
| 2013/0324942 A1 | 12/2013 | de Juan, Jr. et al. | |
| 2014/0031769 A1 | 1/2014 | de Juan, Jr. et al. | |
| 2014/0033800 A1 | 2/2014 | Farinas et al. | |
| 2014/0221941 A1 | 8/2014 | Erickson et al. | |
| 2014/0276482 A1 | 9/2014 | Astafieva et al. | |
| 2014/0296800 A1 | 10/2014 | Erickson et al. | |
| 2014/0358125 A1 | 12/2014 | de Juan, Jr. et al. | |
| 2015/0080846 A1 | 3/2015 | de Juan, Jr. et al. | |
| 2016/0038488 A1 | 2/2016 | Horvath et al. | |
| 2016/0128867 A1 | 5/2016 | Bachelder et al. | |
| 2016/0302965 A1 | 10/2016 | Erickson et al. | |
| 2017/0165108 A1 | 6/2017 | Bianchi et al. | |
| 2019/0117454 A1 | 4/2019 | Campbell et al. | |
| 2020/0113735 A1* | 4/2020 | Kaplan | A61B 17/3211 |
| 2020/0337897 A1 | 10/2020 | Sacherman et al. | |
| 2021/0205130 A1 | 7/2021 | Campbell et al. | |

FOREIGN PATENT DOCUMENTS

| | | | | |
|---|---|---|---|---|
| JP | D1332995 S | 6/2008 | | |
| WO | WO-2011/021225 A1 | 2/2011 | | |
| WO | WO-2016196841 A1 * | 12/2016 | | A61F 9/0017 |

OTHER PUBLICATIONS

U.S. Appl. No. 17/393,059, filed Aug. 3, 2021, 2022/0087863.
U.S. Appl. No. 17/745,007, filed May 16, 2022, 2022/0378609.
U.S. Appl. No. 17/864,120, filed Jul. 13, 2022, 2023/0000676.
U.S. Appl. No. 17/877,643, filed Jul. 29, 2022, 2023/0072346.
U.S. Appl. No. 18/187,898, filed Mar. 22, 2023, 2023/00338282.
U.S. Appl. No. 18/482,689, filed Oct. 6, 2023, 2024/0139027.

* cited by examiner

INCISION GUIDE TOOL FOR OCULAR DEVICE IMPLANTATION AND METHODS OF USE

CROSS-REFERENCES TO RELATED APPLICATIONS

This application is a continuation of PCT/US2023/017929 filed on Apr. 7, 2023, and claims priority to U.S. Provisional Patent Application Ser. No. 63/329,277, filed Apr. 8, 2022, the disclosures of which are hereby incorporated by reference in [its] their entirety for all purposes.

BACKGROUND

Implantable devices can be used to provide a therapeutic agent to one or more locations of a patient. The implantable device may have a reservoir of therapeutic agent, and a structure to retain the implantable device at a desired location of the patient. The implantable device may have a chamber for storing the therapeutic agent, and the agent can be released into the patient to provide a therapeutic benefit. After an amount of time, the amount of fluid released can be less than ideal, and the fluid of the implantable device may be replaced, refilled, or exchanged to provide additional amounts of therapeutic agent to extend the therapy.

Implantable devices for the treatment of the posterior segment of the eye may be implanted through the sclera. As an example, an implantable therapeutic device may be positioned so as to extend from the pars plana region of the eye into the vitreous humor to release the drug directly into the eye. The pars plana region is generally around 3.0 mm to 4.0 mm away from the limbus, which is the border between the cornea and the sclera. To implant the therapeutic device, the conjunctiva may be lifted away, incised, or punctured to access the sclera and an elongate incision created within the sclera. The length of the incision may be critical to whether the device seals with the eye upon insertion through the incision. If the incision is too long the fit between the device and the incision may be off and complications can arise.

Other surgical interventions involve creating of incisions in the sclera including filtration procedures such as trabeculectomy and non-penetrating deep sclerectomy, or implanting a drainage device in the eye to drain aqueous humor from the anterior chamber and thereby reduce the intraocular pressure. In many of these procedures, a scleral flap is surgically formed.

Each of these surgical interventions involve manually performing a cut in the sclera using surgical instruments such as a hand-held blade or knife, which can be technically demanding and time-consuming to achieve a uniform cut that has the appropriate dimensions. There are a number of risks and complications associated with these procedures that can negatively impact the outcome.

SUMMARY

In an aspect, described is a device configured to guide creation of an incision in a sclera of an eye using a cutting blade. The device includes an elongate handle extending along a longitudinal axis for at least a portion of its length and having a proximal end region and a distal end region; and a footplate coupled to the distal end region of the elongate handle. The footplate includes a plurality of struts defining a central opening extending between an upper surface and a lower surface of the footplate. A first strut of the plurality of struts has a proximal-facing blade guide surface that is straight and extends between two lateral struts of the plurality of struts. A second strut of the plurality of struts has a proximal-facing limbal guide surface that is curved. The blade guide surface is separated a distance from the limbal guide surface to identify a target location for creating an incision relative to a limbus of the eye. The blade guide surface has a length between the two lateral struts that limits a length of the incision that can be created between the two lateral struts using a cutting blade inserted through the central opening.

The blade guide surface between the upper and the lower surface of the footplate can extend perpendicular preventing tunneling of the cutting blade relative to the sclera. The blade guide surface can have a radiused portion near the upper surface of the footplate. The blade guide surface below the radiused portion can be between about 0.005" and about 0.020" thick. The blade guide surface can have a chamfered edge near the upper surface of the footplate. The chamfered edge can be between about 10 degrees and about 30 degrees. The distance between the blade guide surface and the limbal guide surface can be about 3.9 mm to about 4.1 mm. The length between the two lateral struts can be about 3.45 mm to about 3.55 mm.

An angle between each of the two lateral struts and the blade guide surface can be about 90 degrees. The two lateral struts can be parallel relative to one another. The footplate can be coupled to the distal end region of the elongate handle at a proximal end region of the footplate near a location of the limbal guide surface. A thickness of the footplate between the upper surface and the lower surface can be less at a distal end region of the footplate near a location of the blade guide surface than a thickness of the footplate between the upper surface and the lower surface near the proximal end region of the footplate. The limbal guide surface can have a chamfered edge near the upper surface of the footplate. Each of the two lateral struts can have a chamfered edge leading into the central opening.

The footplate can be coupled to the distal end region at an angle relative to the longitudinal axis of the elongate handle. The angle can be between 130 degrees and 140 degrees. The elongate handle can further include a shaft between the footplate and the distal end region of the elongate handle. The shaft can extend at an angle relative to the longitudinal axis of the elongate handle that is between 20 degrees and 30 degrees. The first strut can have a distal-facing surface that is curved. The plurality of struts of the footplate can create a shape of a square prism ring, rectangular prism ring, or a trapezoid prism ring.

The lower surface of the footplate can further include a plurality of cleats. The plurality of cleats can include at least a first set of cleats and a second set of cleats, the first set of cleats having an orientation relative to the lower surface that is different from an orientation of the second set of cleats. The first set of cleats can include at least two limbal cleats spaced a distance from one another, each limbal cleat having a shape of a triangular prism with a rectangular base and two rectangular sides that meet forming an elongate lateral edge. Each limbal cleat can lie flush with the limbal guide surface and the lateral edge can be oriented so as to extend in a proximal-to-distal direction relative to the lower surface of the footplate. The second set of cleats can include at least two traction cleats spaced a distance from one another, each of the at least two traction cleats having a shape of a triangular prism with a rectangular base and two rectangular sides that meet forming an elongate lateral edge. The at least two traction cleats can be positioned a distance away from the limbal guide surface. The at least two traction cleats can include two groups of two traction cleats, a first group of two traction cleats positioned on the lower surface of a first lateral strut and a second group of two traction cleats positioned on the lower surface of a second lateral strut. The lateral edge of each traction cleat can be oriented so as to extend orthogonal to the lateral edge of each limbal cleat. The lateral edge of each traction cleat can be oriented so as to extend parallel to the lateral edge of each limbal cleat and orthogonal to the blade guide surface. The plurality of cleats can have a minimum radius of about 0.0015" to prevent penetration and damage to the sclera upon application of a force by the footplate against the eye. The plurality of cleats can be configured to create depressions in the sclera upon application of a force by the footplate against the eye by the device. The plurality of cleats can be configured to resist movement of the footplate during application of a force by a cutting blade along the blade guide surface.

In some variations, one or more of the following can optionally be included in any feasible combination in the above methods, apparatus, devices, and systems. More details of the devices, systems, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally, the figures are not to scale in absolute terms or comparatively but are intended to be illustrative. Also, relative placement of features and elements may be modified for the purpose of illustrative clarity.

It should be appreciated that the drawings herein are for illustration only and are not meant to be to scale.

DETAILED DESCRIPTION

Described herein are guide tools for creating incisions through the surface of the eye with a cutting blade or knife to ensure ideal dimensions of the incisions are achieved such as for implantation of a therapeutic device. The incision guide tools described herein are particularly useful to guide the creation of a scleral incision created using an ophthalmic microvitreoretinal (MVR) blade. An ophthalmic MVR blade is designed to make precise water-tight port in MVR surgery, side ports in small incision cataract surgery, as well as incisions for the insertion of trans-scleral drug delivery devices. In some implementations, the blades are used to create shallow angled "V"-shaped incisions. In other implementations, the blades are used to create generally straight incisions. For example, U.S. Pat. No. 8,808,727 describes insertion of drug delivery devices that are preferably inserted through a straight incision. Slit-shaped incisions are desirable due to their better wound closure with minimal wound leakage of intraocular fluid.

Figure 1A:
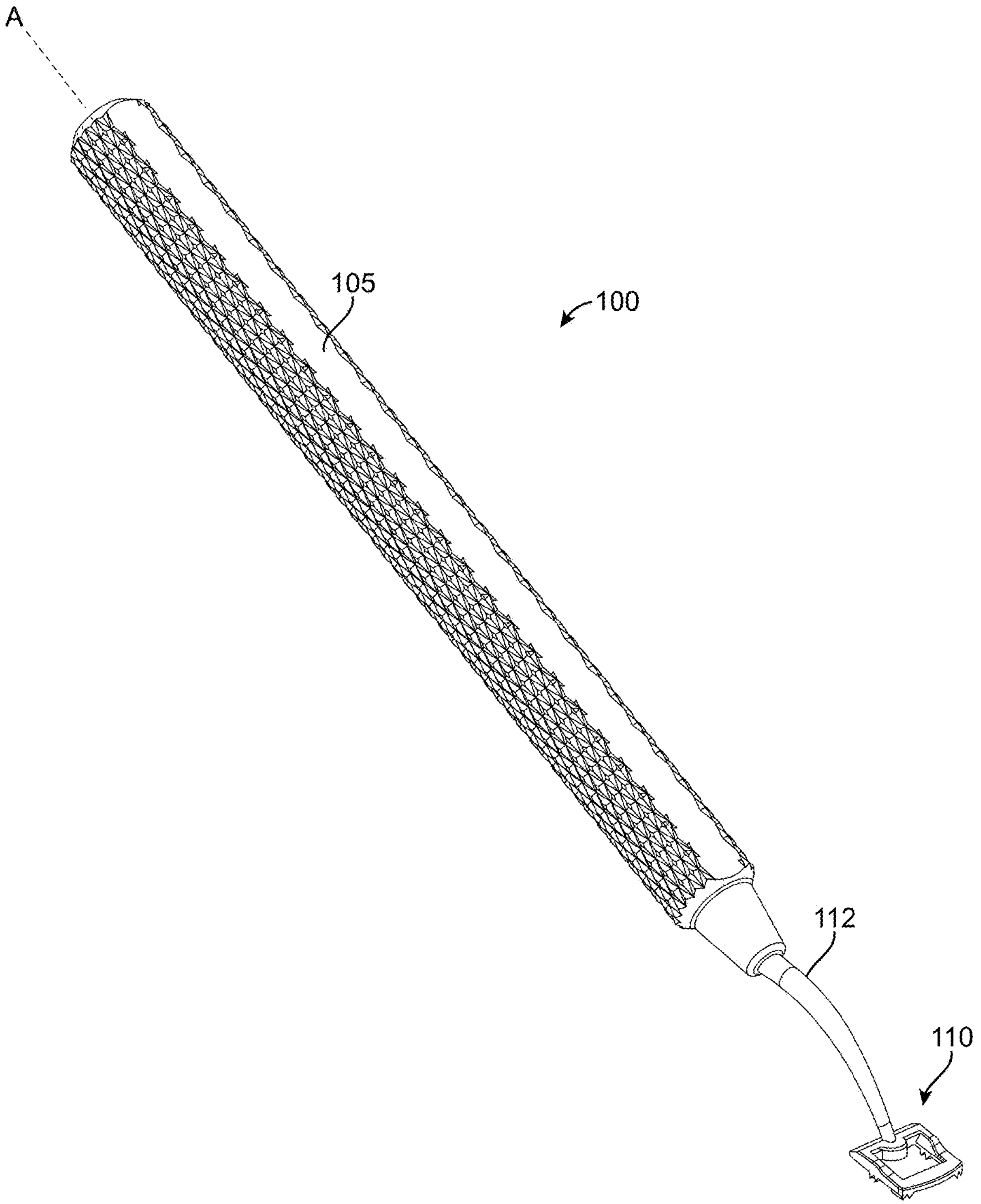
FIG. 1A is a perspective view of an implementation of an incision guide tool.
Figure 1B:
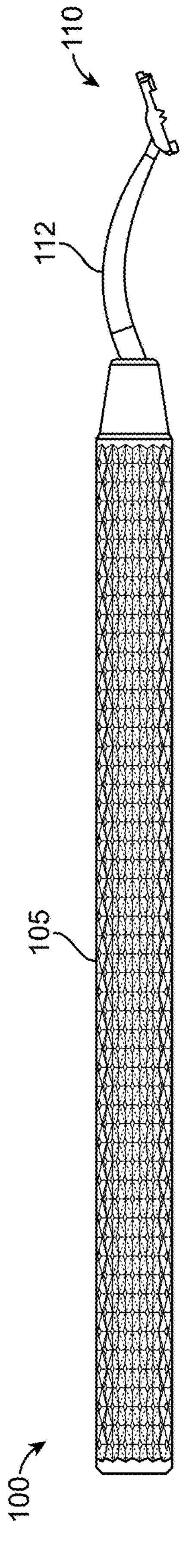
FIGS. 1B and 1C are a side view and a top view, respectively, of the incision guide tool of FIG. 1A.
Figure 1C:
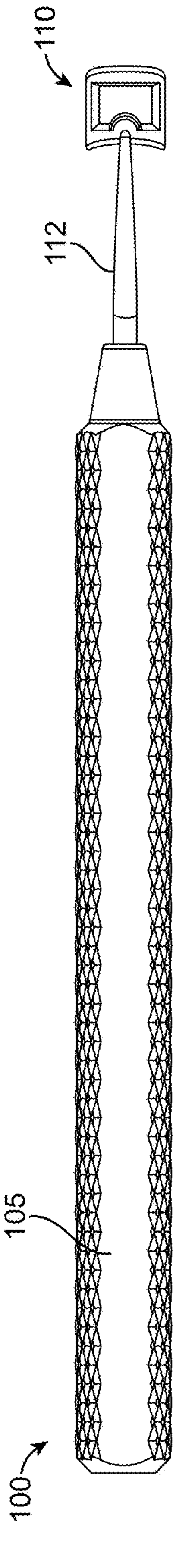

FIG. 1A is a perspective view and FIGS. 1B and 1C are a side view and a top view, respectively, of an implementation of an incision guide tool 100 configured to guide the creation of an incision of an eye using a hand-held cutting blade. Generally, the guide tool 100 includes an elongate handle 105 and a footplate 110 coupled to a distal end region of the elongate handle 105. The handle 105 can extend along a longitudinal axis A for at least a portion of its length. The elongate handle 105 can be coupled to a shaft 112 at a distal end region such that the shaft 112 connects the handle 105 to the footplate 110. Each of the components of the tool 100 will be described in more detail below.

Figure 1D:
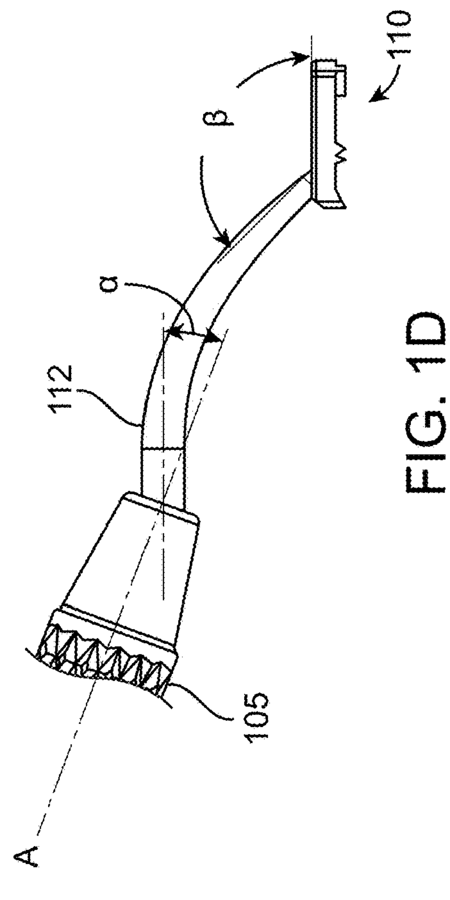
FIG. 1D is a detailed view of the distal end region of the tool of FIG. 1A.

The handle 105, the shaft 112 and the footplate 110 can all be aligned generally with a long axis extending between proximal and distal ends of the tool 100 (see FIG. 1C). The shaft 112 can be angled relative to the handle 105 and/or follow an arced geometry between the handle 105 and the footplate 110 (see FIGS. 1B and 1D). The angle $\alpha$ between the longitudinal axis A of the handle 105 and a first region of the shaft 112 can be between about 20 degrees to about 30 degrees, preferably about 25 degrees. The footplate 110 can be positioned at an angle relative to the handle 105 and also at an angle relative to the distal end region of the shaft 112. The footplate 110 can be coupled to the distal end of the shaft 112 forming an angle $\beta$ between an upper surface of the distal end region of the shaft 112 and the upper surface of the footplate 110. The angle $\beta$ can be between about 130) degrees and about 140 degrees, preferably about 135 degrees. The angles between the shaft 112 and the handle 105 and also the shaft 112 and the footplate 110 provide proper viewing of the target cutting zone of the eye. For example, the arced geometry of the shaft 112 ensures the handle 105 can be placed over a patient's cornea 5 during use without substantial contact or interference (see FIG. 2D).

Figure 6A:
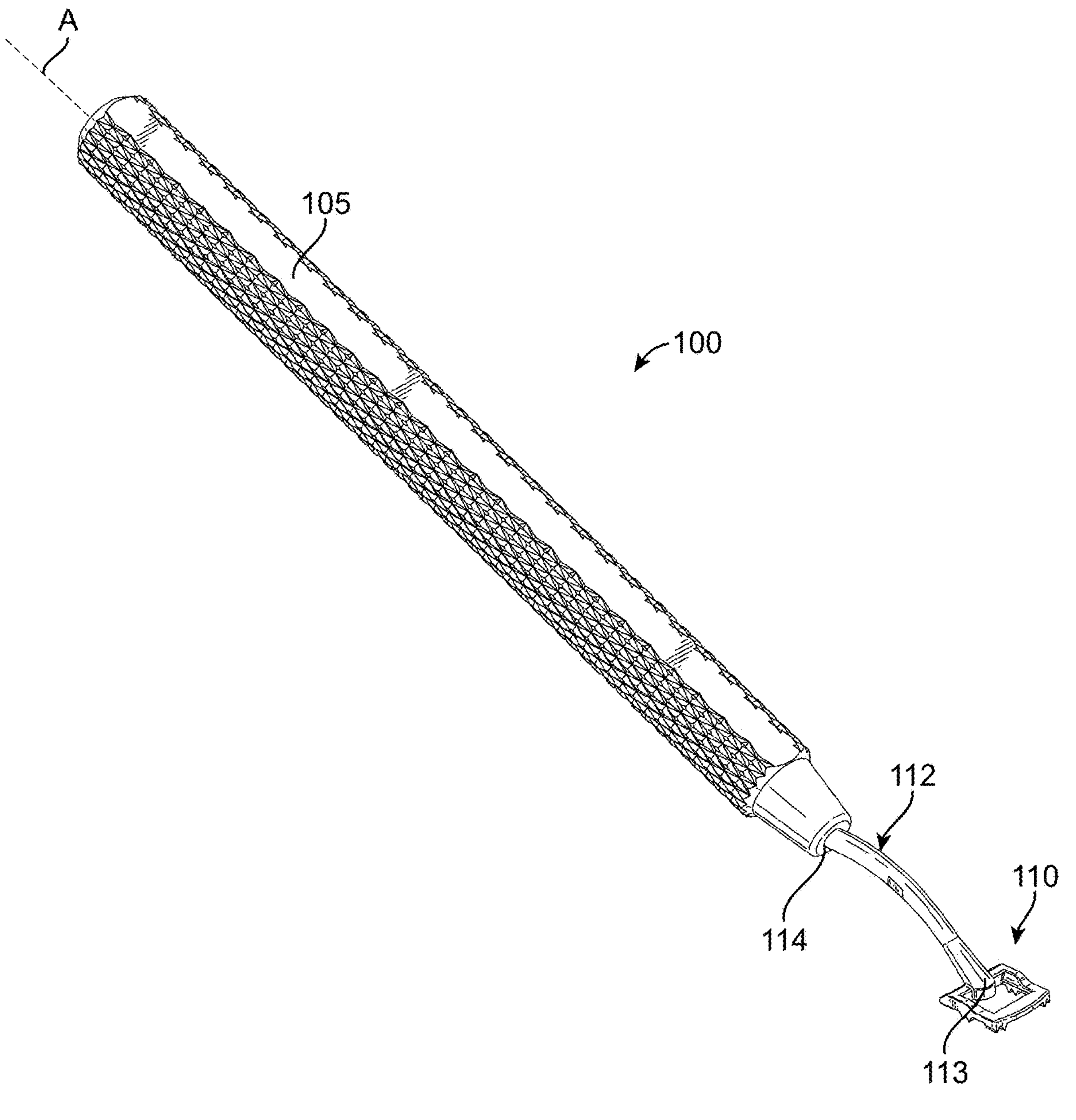
FIG. 6A is a perspective view of an implementation of an incision guide tool.

The implementation of the tool 100 shown in FIGS. 1A-ID illustrate the contour of the shaft 112 being generally rounded. The shaft 112 is also shown in FIGS. 1A-ID tapering from a wider dimension near the proximal end where the shaft 112 is coupled to the handle 105 to a narrower dimension at the distal end near where the shaft 112 is coupled to the footplate 110. The distal end of the shaft 112 need not be narrower where it couples to the footplate 110. The shaft 112 can incorporate a distal end 113 that is at least as wide or wider than the proximal end 114 of the shaft 112 (see FIGS. 6A-6B). The wider dimension of the distal end of the shaft 112 provides good stability for contact with the eye during use.

Figure 2A:
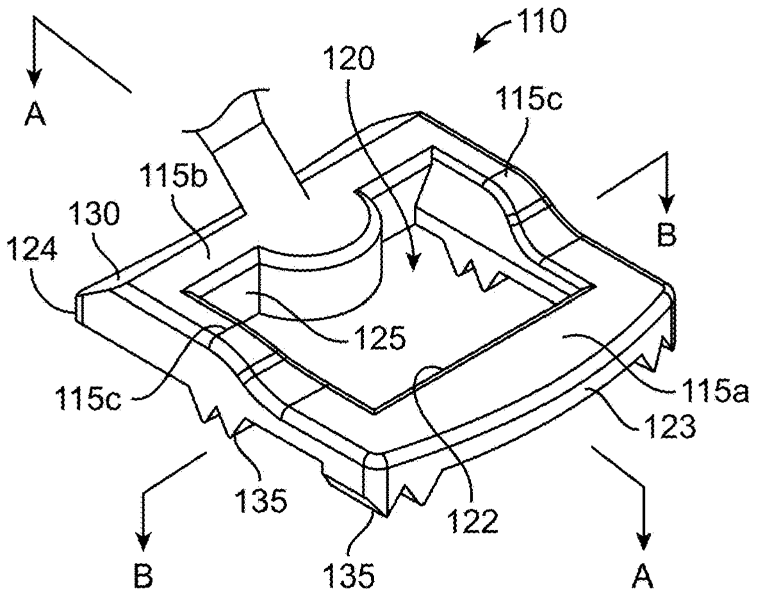
FIG. 2A is a detailed view of an implementation of a footplate.
Figure 2B:
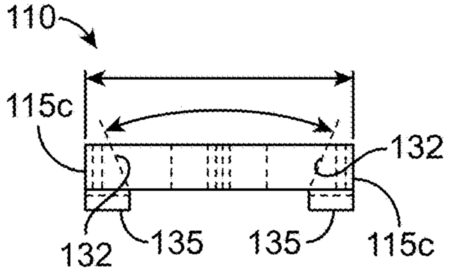
FIG. 2B is a cross-sectional view of the footplate taken along line B-B of FIG. 2A.
Figure 2C:
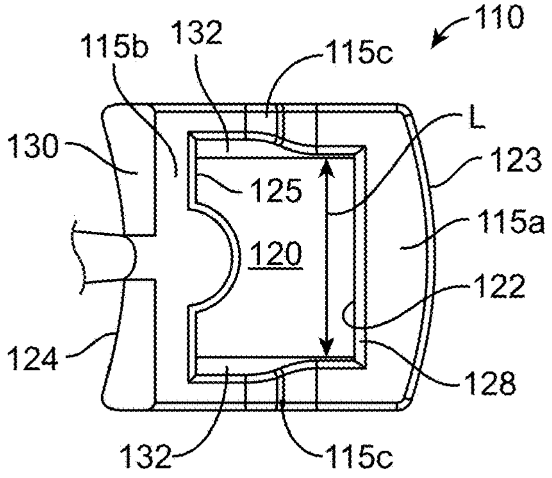
FIG. 2C is a top plan view of the footplate of FIG. 2A.

FIG. 2A is a detailed view of an implementation of a footplate 110. FIG. 2B is a cross-sectional view of the footplate 110 taken along line B-B of FIG. 2A. FIG. 2C is a top plan view of the footplate of FIG. 2A. The footplate 110 can include a plurality of walls or struts 115 arranged to define a central opening 120 extending between an upper surface and a lower surface of the footplate 110. A distal strut 115*a* of the plurality of struts 115 has a proximal-facing blade guide surface 122 and a distal-facing forward surface 123. The blade guide surface 122 is proximal-facing in that it faces towards the location of the coupling between the footplate 110 and the shaft 112, which in the context of a user is in a proximal direction or closer to the user's hand holding the handle 105 of the device 100. The forward surface 123 is distal-facing in that it faces away from the location of the coupling between the footplate 110 and the shaft 112 or away from the user's hand holding the handle 105 of the device 100. A proximal strut 115*b* of the plurality of struts 115 is located opposite the distal strut 115*a* across the central opening 120 and has a proximal-facing limbal guide surface 124 and a distal-facing forward surface 125. Again, the limbal guide surface 124 is proximal-facing in that it faces towards or is nearer to a user's hand holding the handle 105 of the device 100 and the forward surface 125 is distal-facing in that it faces away from the user's hand towards the central opening 120. Both the blade guide surface 122 and the limbal guide surface 124 face in a proximal direction and surfaces 123, 125 of the respective struts 115*a*, 115*b* face in a distal direction.

Still with respect to FIGS. 2A-2C, the blade guide surface 122 of the distal strut 115*a* can be substantially straight from end-to-end whereas the limbal guide surface 124 can be curved from end-to-end. The straight geometry of the blade guide surface 122 is dimensioned for creating a straight scleral incision with a blade 10 (shown in FIG. 2D and as will be discussed in more detail below). The points along the blade guide surface 122 align so as to define a straight line whereas the points along the limbal guide surface 124 do not align and instead follow an arc. It should be noted that terms such as straight should not be regarded as strict or perfect and can include accepted manufacturing tolerances or imperfections. The curved geometry of the limbal guide surface 124 is dimensioned to provide visibility and alignment of the tool 100 with the limbal edge 15 of the eye during use. The arc length of the limbal guide surface 124 can vary, but is preferably about 5.5 mm or sufficient to provide guidance for placing the tool against the limbus or limbal edge 15. The proximal strut 115*b* can also incorporate limbal wings 126 (FIG. 5A-5D) for added length and guidance, if desired.

Figure 2D:
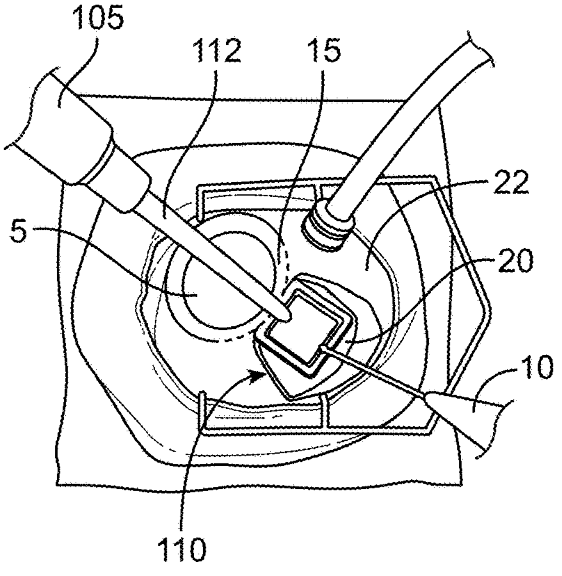
FIG. 2D illustrates positioning of the footplate relative to the limbus of an eye.
Figure 3A:
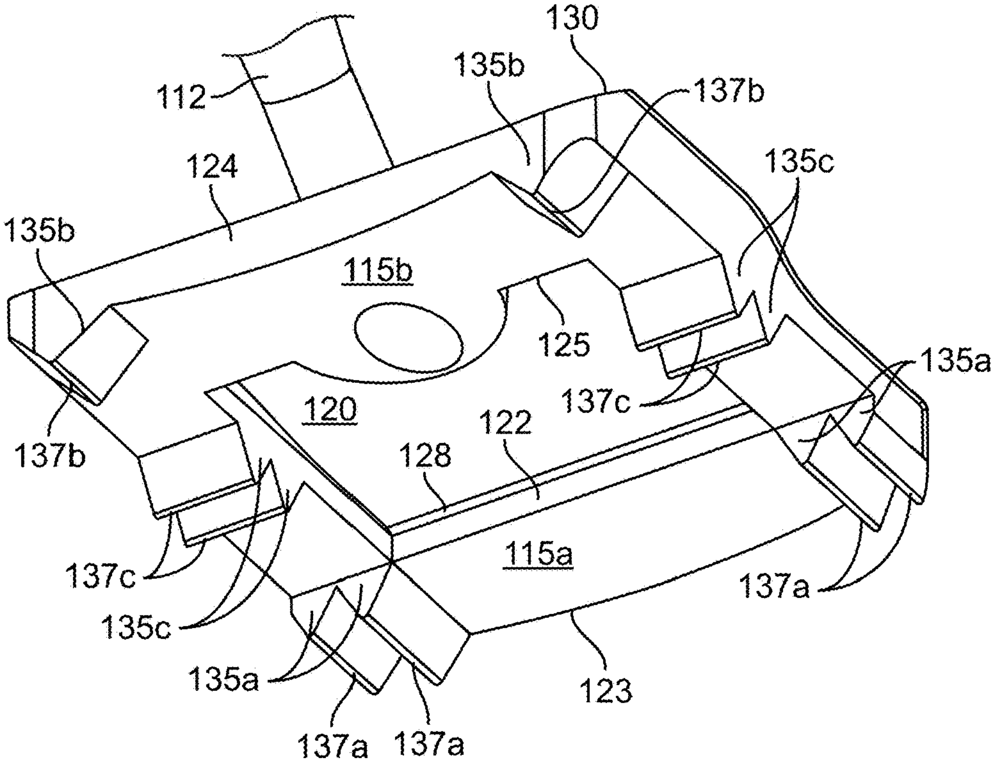
FIG. 3A is a bottom view of the footplate of FIG. 2A.
Figure 3B:
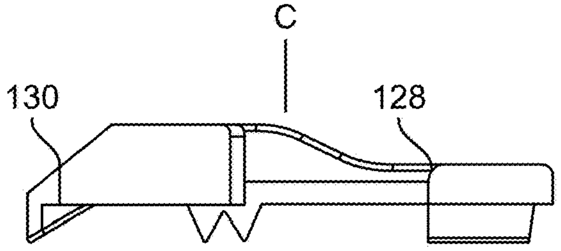
FIGS. 3B-3C are cross-sectional views of the footplate of FIG. 2A taken along line A-A.
Figure 3C:
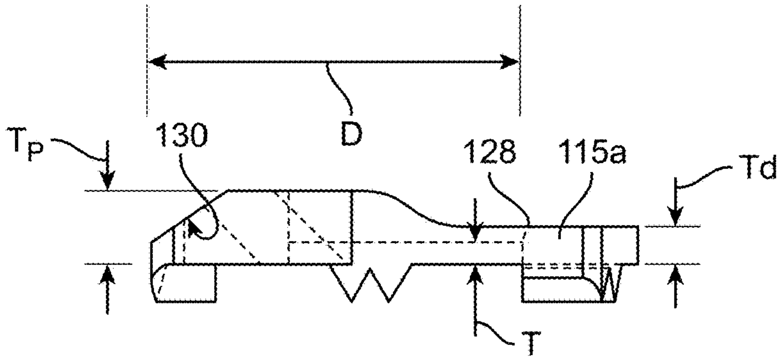

FIG. 2D illustrates the device 100 positioned on a surface of the eye so that the limbal guide surface 124 is aligned with the limbal edge 15. In use, the shaft 112 projects proximally over the cornea 5 when the limbal guide surface 124 is aligned with the limbal edge 15 and the blade guide surface 122 of the footplate 110 extends a distance away onto the sclera 20. The conjunctiva 22 is moved so that the footplate 110 is directly on the sclera, which is located under the conjunctiva 22. FIG. 3A shows the footplate 110 can be coupled to the distal end region of the handle 105 (or the shaft 112) at a proximal end region of the footplate 110 near a location of the limbal guide surface 124. FIG. 3C shows the blade guide surface 122 is separated a distance D from the limbal guide surface 124 to target a location of an incision relative to a limbus of the eye. The distance D can be between about 3.9 mm to about 4.1 mm, preferably about 4.0 mm so that the incision can be formed at the location of the blade guide surface 122 that is preferably about 4.0 mm away from the limbal edge 15. The blade guide surface 122 also has a length L between two lateral struts 115*c* that limits a length of the incision that can be created using a cutting blade inserted through the central opening 120 and slid between the two lateral struts 115*c* (see FIG. 2C). The length L can be between about 3.45 mm to about 3.55 mm, preferably about 3.5 mm so that the incision formed is preferably about 3.5 mm long. The distance D and the length L can be greater than the preferred distance and length, respectively, to account for variability during use.

The distal end of the tool 100 (i.e., the distal-facing forward surface 123 of the distal strut 115*a*) can be curved to clearly distinguish it from the straight blade guide surface 122. The curvature of the limbal guide surface 124 and the curvature of the distal-facing forward surface 123 can be substantially the same. One or more marks, notches, or other visual indicators can be located on an upper surface of the footplate 110 near the blade guide surface 122 to indicate the edge intended to guide cutting versus the edge not intended to guide cutting.

The geometry of the footplate 110 can be substantially rectangular or square in that there may be four struts 115 with the distal and proximal struts 115*a*. 115*b* opposite one another and coupled by a pair of opposing lateral struts 115*c*. The two lateral struts 115*c* can be generally parallel to one another so that the angle between each of the lateral struts 115*c* and the distal strut 115*a* near the blade guide surface 122 is about 90 degrees.

The struts 115 of the footplate 110 preferably form a closed shape having a central opening 120. The two lateral struts 115*c* limit the length of the incision that can be formed along the blade guide surface 122. The blade 10 abuts against the corner and is prevented from creating an incision outside of the desired length. The shape of the plurality of struts 115 with the central opening 120 can be a square prism ring or rectangular prism ring. The closed-ring shape improves visualization of the location of the incision even though the incision is being performed from within the central opening 120 due to the blade guide surface 122 being on a proximal-facing edge of the forward strut 115*a*. This avoids the strut 115*a* from blocking a user's view of the cutting surface. Additionally, the square- or rectangular-shaped prism ring with nearly right angles between each of the struts 115 can improve visualization and access of the blade to the incision site located within the dimensions of the central opening 120. The blade 10 can insert in a first corner (i.e., between the forward strut 115*a* and one of the lateral struts 115*c*) and ensure a full and complete incision is made from end-to-end of the blade guide surface 122 to the opposite corner (i.e., between the forward structure 115*a* and the opposite lateral strut 115*c*).

The footplate 110 can have a geometry that need not include right angles between the struts 115. For example, the footplate 110 can have a plurality of struts 115 that are arranged into a trapezoidal or stadium-shaped or another shape so that the lateral struts 115*c* are non-parallel to one another so that the angle between each of the lateral struts 115*c* and the distal strut 115*a* near the blade guide surface 112 is less than 90 degrees (see FIGS. 5A-5D). In comparison, a prism ring shape having corners near the blade guide surface 122 that are at less than a 90 degree angle, such as a trapezoidal prism ring can impair access of the blade to the incision site at these locations. Angles between the distal strut 115*a* and the lateral struts 115*c* that are less than 90 degrees can hinder alignment of the blade relative to the blade guide surface 122 and impair visualization by a user.

Figure 4A:
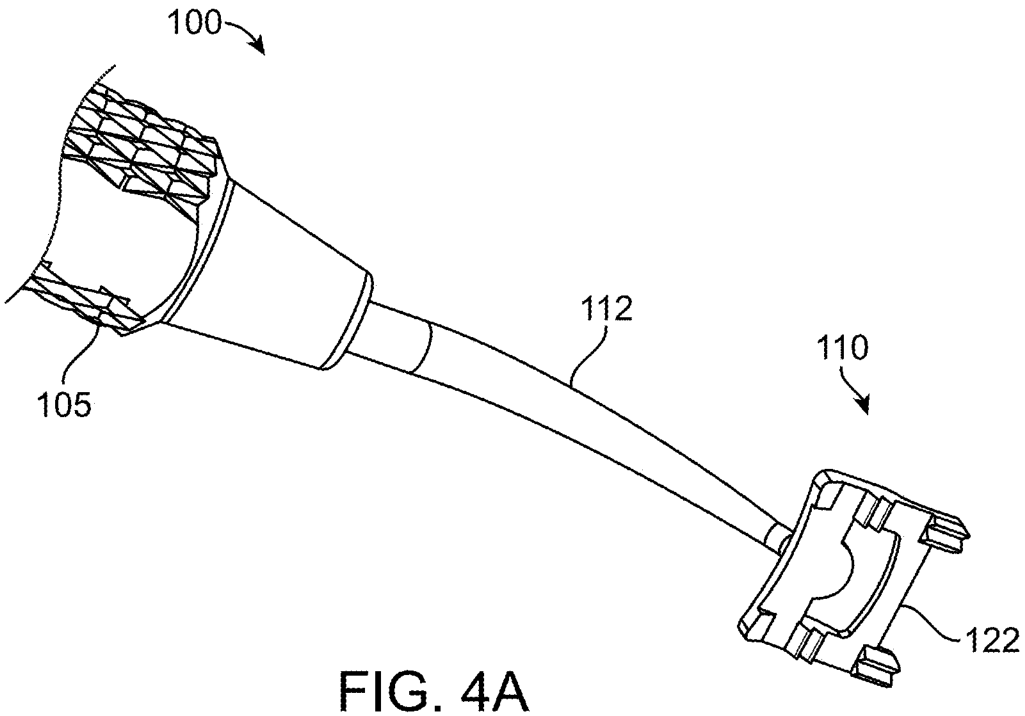
FIGS. 4A-4B are bottom and perspective views of another implementation of an incision guide tool.
Figure 4B:
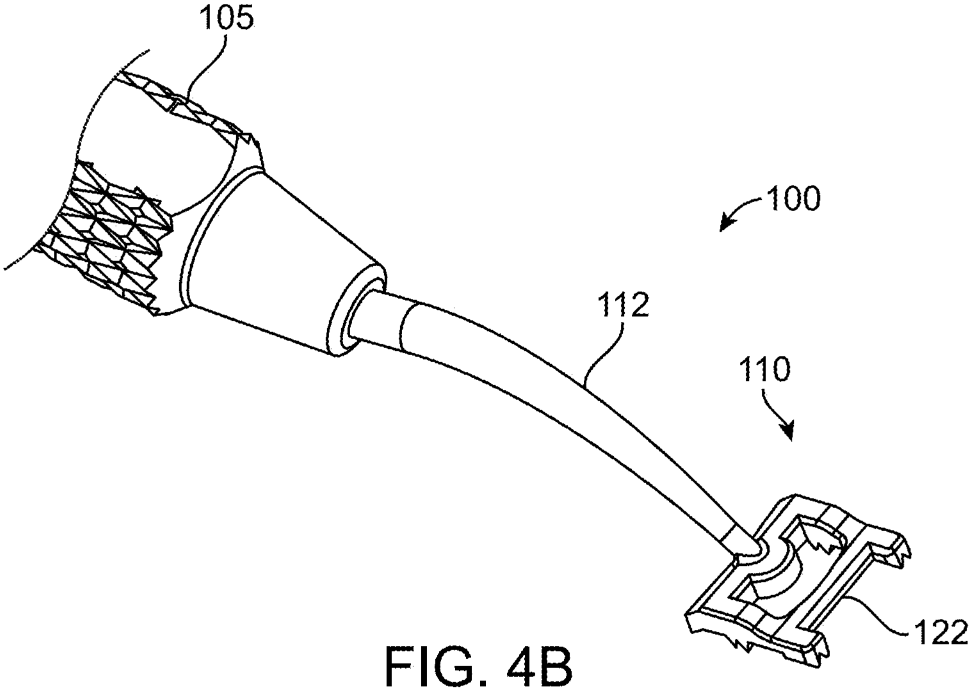
Figure 5A:
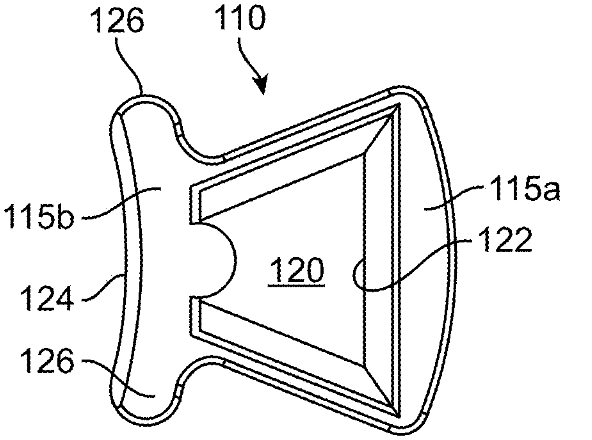
FIG. 5A is a top plan view of another implementation of a footplate.
Figure 5B:
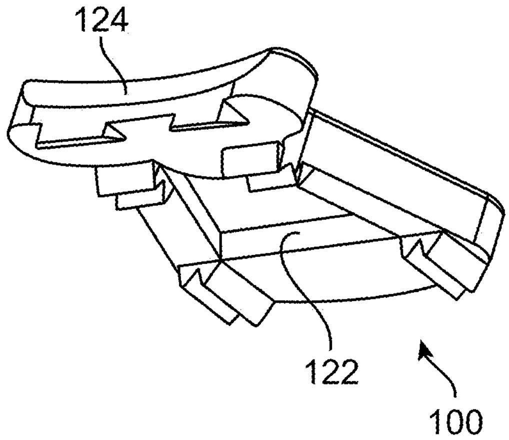
FIGS. 5B-5C are bottom views of the footplate of FIG. 5A.
Figure 5C:
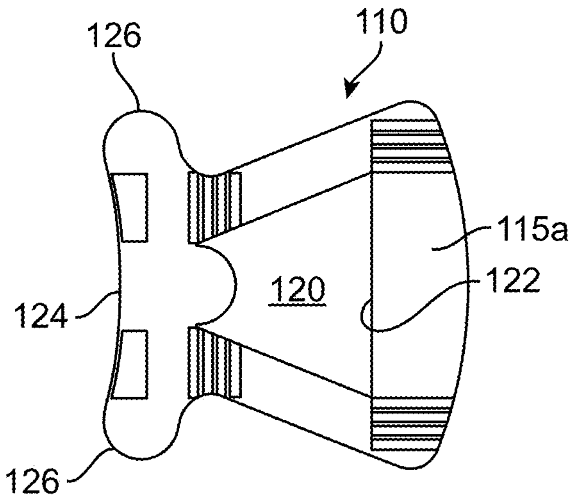
Figure 5D:
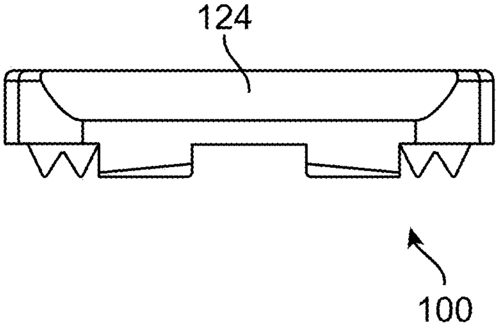
FIG. 5D is a side view of the footplate of FIG. 5A from a proximal end.

In still further implementations, the footplate 110 incorporates a plurality of struts that create a forked shape with an open geometry so that the blade guide surface 122 is located on a distal-facing surface of a strut 115 (see FIGS. 4A-4B).

FIG. 3A is a bottom view of the footplate of FIG. 2A. FIGS. 3B-3C are cross-sectional views of the footplate of FIG. 2A taken along line A-A. The blade guide surface 122 between the upper surface and the lower surface of the footplate 110 can be flat and extend substantially perpendicular to the plane of the central opening 120 or substantially parallel to a central axis C of the central opening 120 extending between the upper and lower surfaces of the footplate 110 (see FIG. 3B). The flat blade guide surface 122 that is substantially parallel to the central axis C encourages perpendicular positioning of the blade relative to the sclera and prevents tunneling or shelving of the blade during creation of the scleral incision.

Generally, the blade 10 approaches the blade guide surface 122 of the footplate 110 from the direction of the distal-facing surface 123 (see FIG. 2D). The blade 10 inserts through the central opening 120 of the footplate 110 so that a flat portion of the blade 10 abuts against the blade guide surface 122 and the sharp blade tip contacts the sclera at a corner between the blade guide surface 122 and a lateral strut 115*c*. The geometry of the blade guide surface 122 ensures the blade 10 can be arranged perpendicular to the surface of the sclera as it inserts through the opening 10 against the surface 122 and along the sclera as it moves laterally along the surface 122.

FIG. 3C shows the blade guide surface 122 can have a radiused portion 128 near the upper surface of the footplate 110. The radiused portion 128 at the upper edge of the guide surface 122 can be between about 0.005" to about 0.010", preferably about 0.008". The blade guide surface 122 below the radiused portion 128 is substantially flat and configured to abut against the flat part of the blade as the blade inserts perpendicularly through the central opening 120. The flat portion of the blade guide surface 122 can have a thickness T that is between about 0.005" and about 0.020" thick, preferably about 0.010". The height of the flat portion and an angle closer to perpendicular significantly reduces the risk of blade tunneling or shelving during use. In other implementations, the blade guide surface 122 has a chamfered edge near the upper surface of the footplate 110 that is between about 10 degrees and about 30 degrees.

The height of the flat portion can be designed to not only encourage blade orientation relative to the sclera, but also to ensure adequate visualization of the incision site and the blade. The footplate 110 can have a proximal end region near where it couples to the handle 105 and a distal end region, for example, closer to a location of the distal strut 115*a* having the blade guide surface 122. The thickness Td of the footplate 110 at the distal end region near a location of the blade guide surface 122 can be minimized so that it is less than a thickness Tp of the footplate 110 near the proximal end region (see FIG. 3C). For example, the thickness Td of the footplate 110 at the distal end can be about 0.015"-0.020" whereas the thickness Tp of the footplate 110 at the proximal end can be about 0.030"-0.035". This change in thickness along the length of the footplate 110 with the thinnest portion near the distal end region of the footplate 110 improves visualization of the incision location and the blade. Minimizing the thickness of this distal strut 115*a* enhances visibility of the incision location. Additionally, the tapered thickness (i.e., Td<Tp) of the footplate 110 allows for enhanced visibility at the corners of the blade guide surface 122. During use, the footplate 110 is positioned against the eye. Depending on the procedure being performed and which eye is being treated, the footplate 110 may be placed in the supero-temporal quadrant such that the handle 105 extends over the cornea of the eye being treated toward the patient's nose. The limbal guide surface 124 is aligned to the limbus and the distal strut 115*a* is directed towards the patient's temple or hair line. A blade can approach the eye from above the footplate 110 and be inserted through the central opening 120 of the footplate 110 so as to incise the eye along the blade guide surface 122 in a generally vertical orientation relative to the scleral surface. The minimized thickness of the distal strut 115*a* minimizes the depth of the window 120 that could otherwise obstruct a surgeon's view of the incision site inside the window 120. The thickness Td is designed to provide good surface area for apposition of the flat part of the blade 10 against the blade guide surface 122 while preventing the footplate from blocking the view of the blade 10 and the incision being created. The thinner distal strut 115*a* and shallower central opening 120 at the location of the blade guide surface 122 provide additional degrees of freedom for the blade, particularly when the blade approaches the corners of the blade guide surface 122. The surgeon can see the incision site more easily and can also rotate, turn, and angle their blade in a desired manner within the opening 120 to achieve a complete cut from corner to corner. The central opening 120 defined on a distal end by a narrower distal strut 115*a* functions as a thin stencil rather than as an obstruction.

Visualization of the limbus 15 can be improved by incorporating a chamfered edge 130 near the upper surface of the footplate 110 leading to the limbal guide surface 124 (see FIGS. 3B-3C). Each of the lateral struts 115*c* also can have a chamfered edge 132 leading into the central opening 120 (see FIGS. 2B-2C). The chamfered edges 132 on the lateral struts 115*c* can accommodate angling of the blade relative to the central opening 120 and to increase visualization of the incision being formed. The chamfered edges 132 of the lateral struts 115*c* can form an angle of about 45 degrees. The angle between the edges 132 and the struts 115 can complement a shape of the blade being used to create the scleral incision. For example, a 45 degree angle complements a diamond-shaped tip of an MVR blade.

Figure 6B:
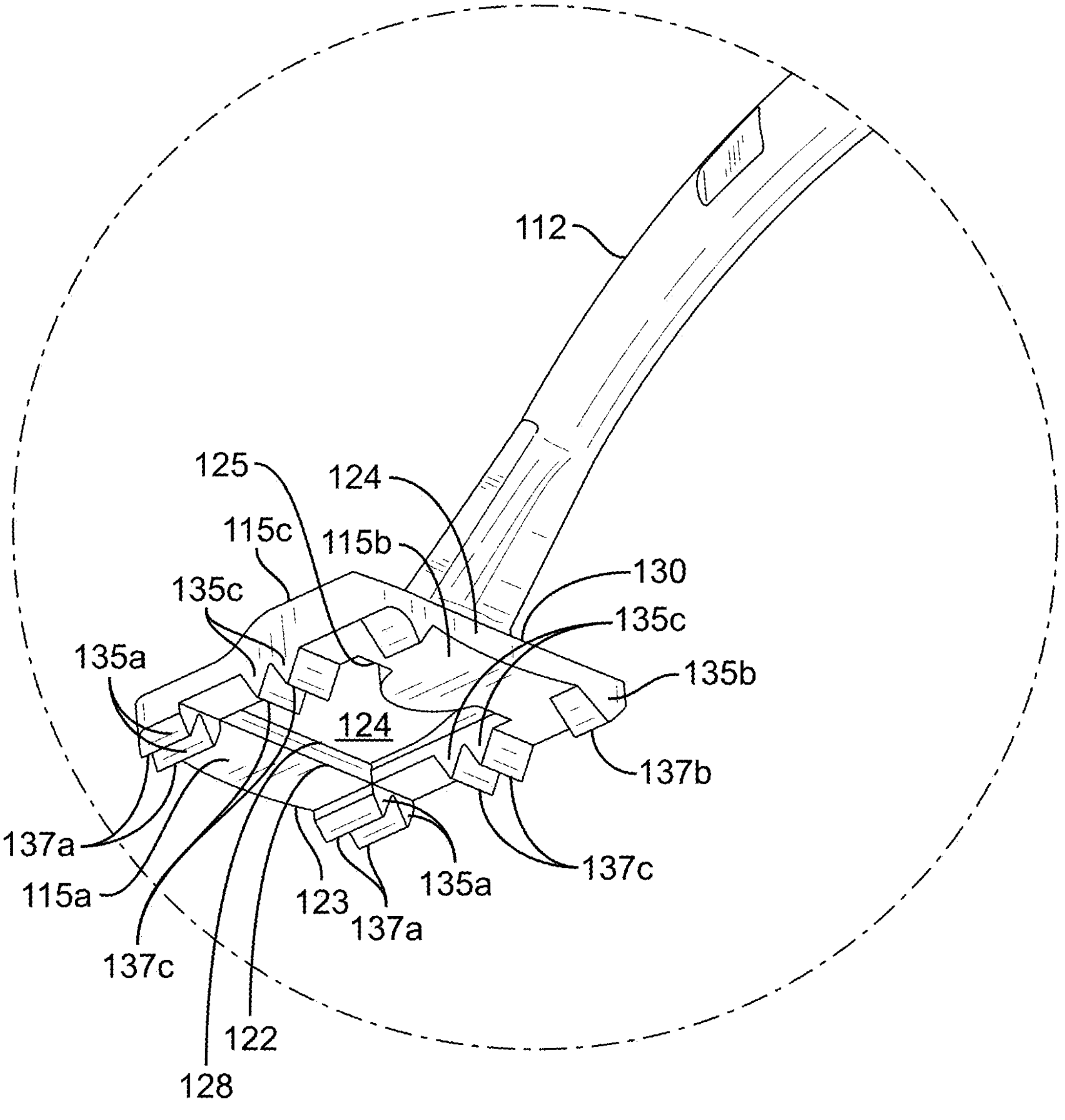
FIG. 6B is a detailed view of the footplate of the incision guide tool of FIG. 6A.

Again with respect to FIG. 3A and also FIG. 6B, the lower surface of the footplate 110 can include a plurality of cleats 135 grouped into different cleat sets 135*a*. 135*b*, 135*c*. Cleat sets 135*a*, 135*c* can be traction cleats and cleat set 135*b* can be limbal cleats. The traction cleats and limbal cleats can be arranged relative to the footplate 110 and relative to each other to provide different functions to the device 100 as will be discussed in more detail below.

At least two traction cleats 135*a* can be positioned near a distal end of the footplate 110 separated a distance from one another. Preferably, at least a first traction cleat 135*a* is positioned at a first location such as near a corner of the blade guide surface 122 where the distal strut 115*a* meets a lateral strut 115*c* and at least a second traction cleat 135*a* is positioned at a second location such as near the opposite corner of the blade guide surface 122 where the distal strut 115*a* meets the opposing lateral strut 115*c*. As such, the span between the first and second traction cleats 135*a* is greater than a width of the central opening 120 and thus, the length L of the blade guide surface 122. The first set of cleats preferably includes two traction cleats 135*a* grouped in the first location and two traction cleats 135*a* grouped in the second location. The first and second locations of the traction cleats 135*a* are preferably distanced further apart than a length of the blade guide surface 122 from lateral strut 115*c* to lateral strut 115*c*. The first and second locations of the traction cleats 135*a* can be arranged further distal relative to the central opening 120 as shown in FIGS. 3A and 6B and/or can be positioned along at least a portion of the lateral struts 115*c* as discussed below.

Each traction cleat 135*a* can have a shape of a triangular prism having a rectangular base and two rectangular sides that meet forming an elongate tip or lateral edge 137*a*. The lateral edge 137*a* creates a non-penetrating spike that provides traction without tissue damage or scleral penetration. The lateral edge 137*a* of each traction cleat 135*a* is oriented so as to extend in a proximal-to-distal direction relative to the lower surface of the footplate 110. The blade guide surface 122 extends laterally in a side-to-side direction. As such, the lateral edge 137*a* of each traction cleat 135*a* is arranged perpendicular to the plane of the blade guide surface 122. This orientation provides grip between the device 100 and the eye even during lateral motion of the blade 10 along the blade guide surface 122.

Still with respect to FIGS. 3A and 6B, the lower surface of the footplate can include a set of limbal cleats 135*b* positioned near the proximal end of the footplate 110 separated a distance from one another. Preferably, at least a first limbal cleat 135*b* is positioned at a first location such as near a corner of the limbal guide surface 124 where the proximal strut 115*b* meets the lateral strut 115*c* and at least a second limbal cleat 135*b* positioned at a second location such as near the opposite corner near where the proximal strut 115*b* meets the opposite lateral strut 115*c*. The span between the first and second limbal cleats 135*b* is generally greater than a width of the central opening 120. The first set of limbal cleats 135*b* preferably includes just one limbal cleat 135*b* in the first location and a second limbal cleat 135*b* in the second location, but more than one limbal cleat per location is also considered herein. The first and second locations of the limbal cleats 135*b* are preferably distanced further apart than a length of the blade guide surface 122 from lateral strut 115*c* to lateral strut 115*c*. The first and second locations of the limbal cleats 135*b* are preferably arranged so that at least one edge of its rectangular base lies flush with the limbal guide surface 124 although they can be positioned further distal.

Each limbal cleat 135*b* can have a shape of a triangular prism having a rectangular base and two rectangular sides that meet forming an elongate lateral edge 137*b*. The lateral edge 137*b* creates a spike that provides traction without penetrating tissue damage. The lateral edge 137*b* of each limbal cleat 135*b* is oriented so as to extend in a proximal-to-distal direction relative to the lower surface of the footplate 110. As such, the lateral edge 137*b* of each limbal cleat 135*b* is arranged perpendicular or orthogonal to the plane of the blade guide surface 122. This orientation provides additional traction of the tool relative to the eye surface even during lateral motion of the blade along the blade guide surface 122. The tool 100 is thus fixed against the surface of the eye even during side-to-side lateral motion of the blade against the blade guide surface 122 to create an incision.

The footplate 110 can incorporate an intermediate group of traction cleats 135*c* positioned on a lower surface of each of the lateral struts 115*c*. This group of traction cleats 135*c* can have their lateral edges 137*c* arranged orthogonal to the lateral edges 137*a* of the other group of traction cleats 135*a* and orthogonal to the lateral edges 137*b* of the limbal cleats 135*b*. FIGS. 3A and 6B shows a first group of traction cleats 135*a* near each corner of the blade guide surface 122 and a second group of traction cleats 135*c* on each lateral strut 115*c*. The lateral edges 137*a* of the first group of traction cleats 135*a* all lie parallel with one another, but orthogonal to the plane of the blade guide surface 122. The lateral edges 137*c* of the second group of traction cleats 135*c* all lie parallel with one another and to the plane of the blade guide surface 122, but are oriented orthogonal to the lateral edges 137*a* of the first group of traction cleats 135*a*.

The geometry of the cleats 135 is configured to provide temporary demarcation of the positioning of the tool 100 on the surface of the eye even after removal of the tool 100. The limbal cleats 135*b*, in particular, demarcate the limbal edge 15 providing guidance for repositioning the tool 100, if desired. The limbal cleats 135*b* are arranged on the lower surface so that one edge of the rectangular base lies flush with the limbal guide surface 124. The lateral edge 137*b* of each of the limbal cleats 135*b* thus ends at the limbal edge 15. The distal traction cleats 135*a* can similarly demarcate the location of the incision site. As discussed above, the traction cleats 135*a* can be arranged at each corner where the distal strut 115*a* meets the lateral strut 115*c* so that the lateral edges 137*b* at each corner identify the location of the incision between them.

Pressing the cleats 135 against the sclera and/or limbus of the eye can indent the surface of the eye so that upon removal of the footplate 110 the indentations left behind can remain visible for a period of time during a procedure. The indentations provide guidance to a user in case the user desires to replace the footplate 110 to the same location according to the same alignment. The indentation acts as temporary markers for aligning the device onto the eye in the same location. The geometry of the cleats is such that they depress the sclera upon application of a force on the footplate 110, but do not penetrate the sclera. There is at least some rounding at the lateral edges 137 of the cleats 135 so as to avoid penetrating or cutting tissue that would occur with a sharp needle point or blade point. The unique orientation of the sets of cleats relative to one another as well as relative to the blade guide surface provide guidance as to the location of the limbus and the location of the incision site. The indentations left behind by the cleats mirror this pattern and help to arrange the footplate onto the surface of the eye in the correct orientation.

The minimum radii at the lateral edges 137 of all the footplate cleats 135 is about 0.0015". This minimum radius ensures the cleats 135 are not sharp and avoid penetrating the scleral surface of the eye. Each cleat 135 extends away from the lower surface of the footplate 110 to a height of between about 0.015" to about 0.025". The width of each cleat along its base can be between about 0.035" to about 0.050". The lateral edges 137 of each cleat 135 has a corresponding dimension so that they contact the sclera along a corresponding length to the width of each cleat base. The limbal cleats 135*b* can form an interior angle of about 90 degrees whereas the traction cleats 135*a*, 135*c* can form an interior angle of about 60 degrees. The number, shape, arrangement, spacing, and groupings of the cleats can vary. Where groups of two cleats are described, the groups can be of three or more cleats or just one cleat each.

Suitable materials or combinations of materials for the preparation of the various components of the devices disclosed herein are provided throughout. It should be appreciated that other suitable materials are considered. The device can be constructed from any medical grade material that can provide the functions required of the component. Materials that may be employed in this device include materials compatible with standard sterilization processes by autoclave or pressurized steam treatment such as a titanium alloy, stainless steel, or other medical grade materials. The device may be made from a combination of materials that are geometrically mated together, chemically bonded or welded to one another, overmolded, encapsulated, or other means for joining multiple materials. A given device element may be made of multiple materials. The different components (i.e., the handle 105, shaft 112, and footplate 110) can be formed of the same material or materials or can be formed of different materials. In some implementations, the handle 105 is formed of a metal material and the shaft 112 and footplate 110 are formed of polymer material(s). The shaft 112 and footplate 110 can be injection molded polymer integrated as a single component configured to be coupled to the distal end of the handle 105.

Methods of Use

An example of the device 100 used during an implantation procedure is provided below. The conjunctiva and Tenon's capsule may be dissected into a fornix based flap at the limbus and superficial and minimum wet-field cautery may be applied on perforating blood-vessels, if necessary. Hemostasis of the scleral surface is verified and any excess blood from the scleral surface cleared. Wet-field cauterization may be performed particularly in the area of the sclera-pars plana incision. After cautery, the surface of the eye is dried with a cotton tipped applicator or sponge. The curved limbal guide surface 124 of the footplate 110 is aligned to the limbus 15 at the supero-temporal quadrant. The footplate 110 is placed flat on the eye so that the cleats 135 provide stable positioning against the sclera 20. While maintaining the plate 110 flat against the sclera 20, the globe of the eye can be rotated using the device 100, if necessary, to visualize the inner blade guide surface 122 through the central opening 120. A blade 10 such as a microvitreoretinal (MVR) blade can be inserted through the central opening 120 so that the sharp point of the blade 10 is placed at a first corner of the blade guide surface 122 and the flat side of the blade hugs against the blade guide surface 122. The sclera 20 can be gently dissected by tracing the blade 10 flat against and along the blade guide surface 122 to the opposite corner using multiple light passes in the same direction while ensuring the blade 10 is substantially perpendicular to the surface of the eye. After the initial cut is performed using the device 100 as a guide, a full thickness dissection of the sclera 20 is performed using the blade 10 until the pars plana is fully visible. The full thickness incision can be performed with the device 100 in place or after the device 100 is removed. If the device 100 is removed, the full thickness incision should be performed without extending the incision beyond a length of this initial guided cut. The final scleral dissection length is preferably about 3.5 mm and a full thickness perpendicular through the sclera 20. If desired, the device 100 can be placed again onto the eye using the indentations left by the cleats 135 to orient the device 100 into the same position relative to the eye.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detain in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various placed throughout this specification are not necessarily referring to the same embodiment or implementation. Furthermore, the particular features, structures, configurations, or characteristics may be combined in any suitable manner in one or more implementations.

The devices and systems described herein can incorporate any of a variety of features. Elements or features of one implementation of a device and system described herein can be incorporated alternatively or in combination with elements or features of another implementation of a device and system described herein. For the sake of brevity, explicit descriptions of each of those combinations may be omitted although the various combinations are to be considered herein. Additionally, the devices and systems described herein can be positioned in the eye and need not be implanted specifically as shown in the figures or as described herein. The various devices can be implanted, positioned and adjusted etc. according to a variety of different methods and using a variety of different devices and systems. The various devices can be adjusted before, during as well as any time after implantation. Provided are some representative descriptions of how the various devices may be implanted and positioned, however, for the sake of brevity explicit descriptions of each method with respect to each implant or system may be omitted.

The use of relative terms throughout the description may denote a relative position or direction or orientation and is not intended to be limiting. For example, "distal" may indicate a first direction away from a reference point. Similarly, "proximal" may indicate a location in a second direction opposite to the first direction. Use of the terms "upper," "lower," "top", "bottom," "front," "side," and "back" as well as "anterior," "posterior," "caudal," "cephalad" and the like or used to establish relative frames of reference, and are not intended to limit the use or orientation of any of the devices described herein in the various implementations.

As used herein, the term "about" means a range of values including the specified value, which a person of ordinary skill in the art would consider reasonably similar to the specified value. In aspects, about means within a standard deviation using measurements generally acceptable in the art. In aspects, about means a range extending to +/−10% of the specified value. In aspects, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A device configured to guide creation of an incision in a sclera of an eye using a cutting blade, the device comprising:

an elongate handle extending along a longitudinal axis for at least a portion of its length and having a proximal end region and a distal end region; and a footplate coupled to the distal end region of the elongate handle, the footplate comprising a plurality of struts defining a central opening extending between an upper surface and a lower surface of the footplate, wherein a first strut of the plurality of struts has a proximal-facing blade guide surface that is straight and extends between two lateral struts of the plurality of struts, and wherein a second strut of the plurality of struts has a proximal-facing limbal guide surface defining an arc about a center point positioned proximal to the proximal-facing limbal guide surface, wherein the blade guide surface is separated a distance from the limbal guide surface to identify a target location for creating an incision relative to a limbus of the eye, and wherein the blade guide surface has a length between the two lateral struts that limits a length of the incision that can be created between the two lateral struts using a cutting blade inserted through the central opening.

2. The device of claim 1, wherein the blade guide surface between the upper surface and the lower surface of the footplate extends perpendicular preventing tunneling of the cutting blade relative to the sclera.

3. The device of claim 2, wherein the blade guide surface has a radiused portion near the upper surface of the footplate.

4. The device of claim 3, wherein the blade guide surface below the radiused portion is between about 0.005" and about 0.020" thick.

5. The device of claim 2, wherein the blade guide surface has a chamfered edge near the upper surface of the footplate.

6. The device of claim 5, wherein the chamfered edge is between about 10 degrees and about 30 degrees.

7. The device of claim 1, wherein the distance between the blade guide surface and the limbal guide surface is about 3.9 mm to about 4.1 mm.

8. The device of claim 1, wherein the length between the two lateral struts is about 3.45 mm to about 3.55 mm.

9. The device of claim 1, wherein an angle between each of the two lateral struts and the blade guide surface is about 90 degrees.

10. The device of claim 9, wherein the two lateral struts are parallel relative to one another.

11. The device of claim 1, wherein the footplate is coupled to the distal end region of the elongate handle at a proximal end region of the footplate near a location of the limbal guide surface.

12. The device of claim 11, wherein a thickness of the footplate between the upper surface and the lower surface is less at a distal end region of the footplate near a location of the blade guide surface than a thickness of the footplate between the upper surface and the lower surface near the proximal end region of the footplate.

13. The device of claim 1, wherein the limbal guide surface has a chamfered edge near the upper surface of the footplate.

14. The device of claim 1, wherein each of the two lateral struts has a chamfered edge leading into the central opening.

15. The device of claim 1, wherein the footplate is coupled to the distal end region at an angle relative to the longitudinal axis of the elongate handle.

16. The device of claim 15, wherein the angle is between 130 degrees and 140 degrees.

17. The device of claim 1, wherein the elongate handle further comprises a shaft between the footplate and the distal end region of the elongate handle.

18. The device of claim 17, wherein the shaft extends at an angle relative to the longitudinal axis of the elongate handle that is between 20 degrees and 30 degrees.

19. The device of claim 1, wherein the first strut has a distal-facing surface that is curved.

20. The device of claim 1, wherein the plurality of struts of the footplate creates a shape of a square prism ring, rectangular prism ring, or a trapezoid prism ring.

21. The device of claim 1, wherein the lower surface of the footplate further comprises a plurality of cleats.

22. The device of claim 21, wherein the plurality of cleats has a minimum radius of about 0.0015" to prevent penetration and damage to the sclera upon application of a force by the footplate against the eye.

23. The device of claim 22, wherein the plurality of cleats is configured to create depressions in the sclera upon application of a force by the footplate against the eye by the device.

24. The device of claim 21, wherein the plurality of cleats is configured to resist movement of the footplate during application of a force by a cutting blade along the blade guide surface.

25. The device of claim 21, wherein the plurality of cleats comprises at least a first set of cleats and a second set of cleats, the first set of cleats having an orientation relative to the lower surface that is different from an orientation of the second set of cleats.

26. The device of claim 25, wherein the first set of cleats comprises at least two limbal cleats spaced a distance from one another, each limbal cleat having a shape of a triangular prism with a rectangular base and two rectangular sides that meet forming an elongate lateral edge.

27. The device of claim 26, wherein each limbal cleat lies flush with the limbal guide surface and the lateral edge is oriented so as to extend in a proximal-to-distal direction relative to the lower surface of the footplate.

28. The device of claim 27, wherein the second set of cleats comprises at least two traction cleats spaced a distance from one another, each of the at least two traction cleats having a shape of a triangular prism with a rectangular base and two rectangular sides that meet forming an elongate lateral edge.

29. The device of claim 28, wherein the at least two traction cleats are positioned a distance away from the limbal guide surface.

30. The device of claim 29, wherein the at least two traction cleats comprises two groups of two traction cleats, a first group of two traction cleats positioned on the lower surface of a first lateral strut and a second group of two traction cleats positioned on the lower surface of a second lateral strut.

31. The device of claim 29, wherein the lateral edge of each traction cleat is oriented so as to extend orthogonal to the lateral edge of each limbal cleat.

32. The device of claim 29, wherein the lateral edge of each traction cleat is oriented so as to extend parallel to the lateral edge of each limbal cleat and orthogonal to the blade guide surface.

33. A device configured to guide creation of an incision in a sclera of an eye using a cutting blade, the device comprising:

an elongate handle extending along a longitudinal axis for at least a portion of its length and having a proximal end region and a distal end region; and a footplate coupled to the distal end region of the elongate handle, the footplate comprising a plurality of struts defining a central opening extending between an upper surface and a lower surface of the footplate, wherein a first strut of the plurality of struts has a proximal-facing blade guide surface that is straight and extends between two lateral struts of the plurality of struts, and wherein a second strut of the plurality of struts has a proximal-facing limbal guide surface that is curved, wherein the blade guide surface is separated a distance from the limbal guide surface to identify a target location for creating an incision relative to a limbus of the eye, wherein the blade guide surface has a length between the two lateral struts that limits a length of the incision that can be created between the two lateral struts using a cutting blade inserted through the central opening, and wherein each of the two lateral struts has a chamfered edge leading into the central opening.

34. A device configured to guide creation of an incision in a sclera of an eye using a cutting blade, the device comprising:

an elongate handle extending along a longitudinal axis for at least a portion of its length and having a proximal end region and a distal end region; and a footplate coupled to the distal end region of the elongate handle, the footplate comprising a plurality of struts defining a central opening extending between an upper surface and a lower surface of the footplate, wherein a first strut of the plurality of struts has a proximal-facing blade guide surface that is straight and extends between two lateral struts of the plurality of struts, and wherein a second strut of the plurality of struts has a proximal-facing limbal guide surface that is curved, wherein the blade guide surface is separated a distance from the limbal guide surface to identify a target location for creating an incision relative to a limbus of the eye, wherein the blade guide surface has a length between the two lateral struts that limits a length of the incision that can be created between the two lateral struts using a cutting blade inserted through the central opening, wherein the lower surface of the footplate further comprises a plurality of cleats; and wherein the plurality of cleats comprises at least a first set of cleats and a second set of cleats, the first set of cleats having an orientation relative to the lower surface that is different from an orientation of the second set of cleats.

* * * * *